/

US008178084B2

(12) United States Patent
Smith et al.

(10) Patent No.: US 8,178,084 B2
(45) Date of Patent: May 15, 2012

(54) PHARMACEUTICAL KITS COMPRISING MESENCHYMAL STEM CELLS

(75) Inventors: Roger Kenneth Whealands Smith, Hatfield (GB); Kenneth Gregory McGarrell, Hatfield (GB); Allen Edward Goodship, Hatfield (GB); Gordon William Blunn, Middlesex (GB)

(73) Assignee: Quy Biosciences Limited, Chipping Norton (GB)

( * ) Notice: Subject to any disclaimer, the term of this patent is extended or adjusted under 35 U.S.C. 154(b) by 1509 days.

(21) Appl. No.: 10/526,753

(22) PCT Filed: Sep. 8, 2003

(86) PCT No.: PCT/GB03/03894
§ 371 (c)(1),
(2), (4) Date: Sep. 14, 2005

(87) PCT Pub. No.: WO2004/022078
PCT Pub. Date: Mar. 18, 2004

(65) Prior Publication Data
US 2006/0130852 A1 Jun. 22, 2006

(30) Foreign Application Priority Data

Sep. 7, 2002 (GB) .................................. 0220841.1
Nov. 12, 2002 (GB) .................................. 0226275.6

(51) Int. Cl.
*A01N 63/00* (2006.01)
*A01N 65/00* (2009.01)
*C12N 5/00* (2006.01)
*C12N 5/02* (2006.01)
(52) U.S. Cl. ....... 424/93.1; 424/93.7; 435/383; 435/405
(58) Field of Classification Search .................. 424/93.1
See application file for complete search history.

(56) References Cited

U.S. PATENT DOCUMENTS

| 5,226,914 | A | | 7/1993 | Caplan et al. |
| 5,486,359 | A | | 1/1996 | Caplan et al. |
| 5,733,542 | A | | 3/1998 | Haynesworth et al. |
| 5,811,094 | A | * | 9/1998 | Caplan et al. ................. 424/93.7 |
| 5,874,500 | A | | 2/1999 | Rhee et al. |
| 5,906,934 | A | | 5/1999 | Grande et al. |
| 6,010,696 | A | | 1/2000 | Caplan et al. |
| 6,087,113 | A | | 7/2000 | Caplan et al. |
| 6,200,606 | B1 | | 3/2001 | Peterson et al. |
| 6,214,369 | B1 | | 4/2001 | Grande et al. |
| 6,280,473 | B1 | * | 8/2001 | Lemperle et al. .......... 623/16.11 |
| 6,835,377 | B2 | * | 12/2004 | Goldberg et al. ............ 424/93.7 |
| 2002/0045260 | A1 | | 4/2002 | Hung et al. |
| 2002/0110544 | A1 | | 8/2002 | Goldberg et al. |
| 2002/0123143 | A1 | | 9/2002 | Toma et al. |
| 2004/0151703 | A1 | | 8/2004 | Ha et al. |

FOREIGN PATENT DOCUMENTS

| WO | 96/28539 | 9/1996 |
| WO | WO 98/51317 | 11/1998 |
| WO | 99/03973 | 1/1999 |
| WO | 99/46366 | 9/1999 |
| WO | 00/06701 | 2/2000 |
| WO | 00/49136 | 8/2000 |
| WO | WO 01/26667 | 4/2001 |
| WO | WO 01/34775 | 5/2001 |
| WO | 01/70290 | 9/2001 |
| WO | WO 01/80865 | 11/2001 |
| WO | 02/34889 | 5/2002 |
| WO | WO 03/015802 | 2/2003 |

OTHER PUBLICATIONS

Sutter, 2007, Clinical Techniques in Equine Practice, 2007, 6:198-208.*
Jorgenson, Ann Rheum Dis 2001, 60:305-309.*
Krampera, Bone, 2006, 39:678-683.*
Redman, European Cells and Materials, 2005, 9:23-32.*
Eibes et al, Jour Biotechnol, 2010, 146:194-197.*
Awad et al (1999) Tissue Engineering 5:267-277.
Bruder et al (1994) J Cell Biochem 56:283-294.
Caplan and Bruder (2001) Trends Mol Med 7:259-264.
Caplan et al (1993), in "The Anterior Cruciate Ligament: Current and Future Concepts", Jackson, Ed., Raven Press, Ltd., New York, pp. 405-417.
Carter et al (1998) Clinical Orthopaedics and Related Research 355 Suppl:S51-55.
Cauvin (2001) "An investigation into the roles of transforming growth factor-beta (TGFB) in the development, adaptation, and repair of equine tendons." PhD Thesis, Royal Veterinary College, University of London.
Dahlgren et al (2001) Am J Vet Res 62:1557-1562.
Dowling et al (2000) Equine Vet J 32:369-378.
Dyson (2000) Proc Am Assoc Equine Practnrs 46:137-142.
Dyson et al (1995) Vet Clin North Am: Equine Practice 11:177-215.
Genovese (1992) Proc Am Assoc Equine Practnrs 28:265-272.
Herthel (2001) Proc Am Assoc Equine Practnrs 47:319-321.
Hildebrand et al (2002) Microse Res Tech 58:34-38.
Kato et al (1991)J Bone Joint Surg 73-A:561-574.
MacKenzie et al (2000) Blood 96:763a, Abstract #3299.
Reef et al (1996), in "Proceedings of the First Dubai International Equine Symposium. The Equine Athlete: Tendon, Ligament, and Soft Tissue Injuries", Rantanen and Hauser, Eds,, Dubai, M R Rantanen Design, pp. 413-430.
Reef et al (1997) Proc Am Assoc Equine Practnrs 43:301-305.
Rickard et al (1996) J Bone Min Res 11:312-324.
Ringe et al (2002) Die Naturwissenchaftan 89:338-351.
Smith et al (1994) Equine Vet J 26:460-465.
Wakitani et al (1994) J Bone Joint Surg 76-A:579-592.
Watanabe et al (2002) Microscopy Research and Technique 58:39-44.
Woo et al (1999) Clinical Orthopaedics and Related Research 367 Suppl:S312-323.
Young et al (1998) J Orthop Res 16:406-413.
Godwin et al., Implantation of bone marrow-derived mesenchymal stem cells demonstrates improved outcome in horses with over-strain injury of the superficial digital flexor tendon, Equine Veterinary Journal, 2011.

(Continued)

*Primary Examiner* — Valarie Bertoglio
(74) *Attorney, Agent, or Firm* — Klauber & Jackson LLC

(57) ABSTRACT

A method of treating a natural soft skeletal tissue injury in a patient the method comprising administering to the patient a composition of mesenchymal stem cells in liquid suspension enriched compared to the natural source of said cells, or tenocytes derived therefrom. The method is particularly suited to the regeneration of tendons in competitive mammals, such as the superficial digital flexor tendon of the horse.

23 Claims, 9 Drawing Sheets

OTHER PUBLICATIONS

Figure 1:
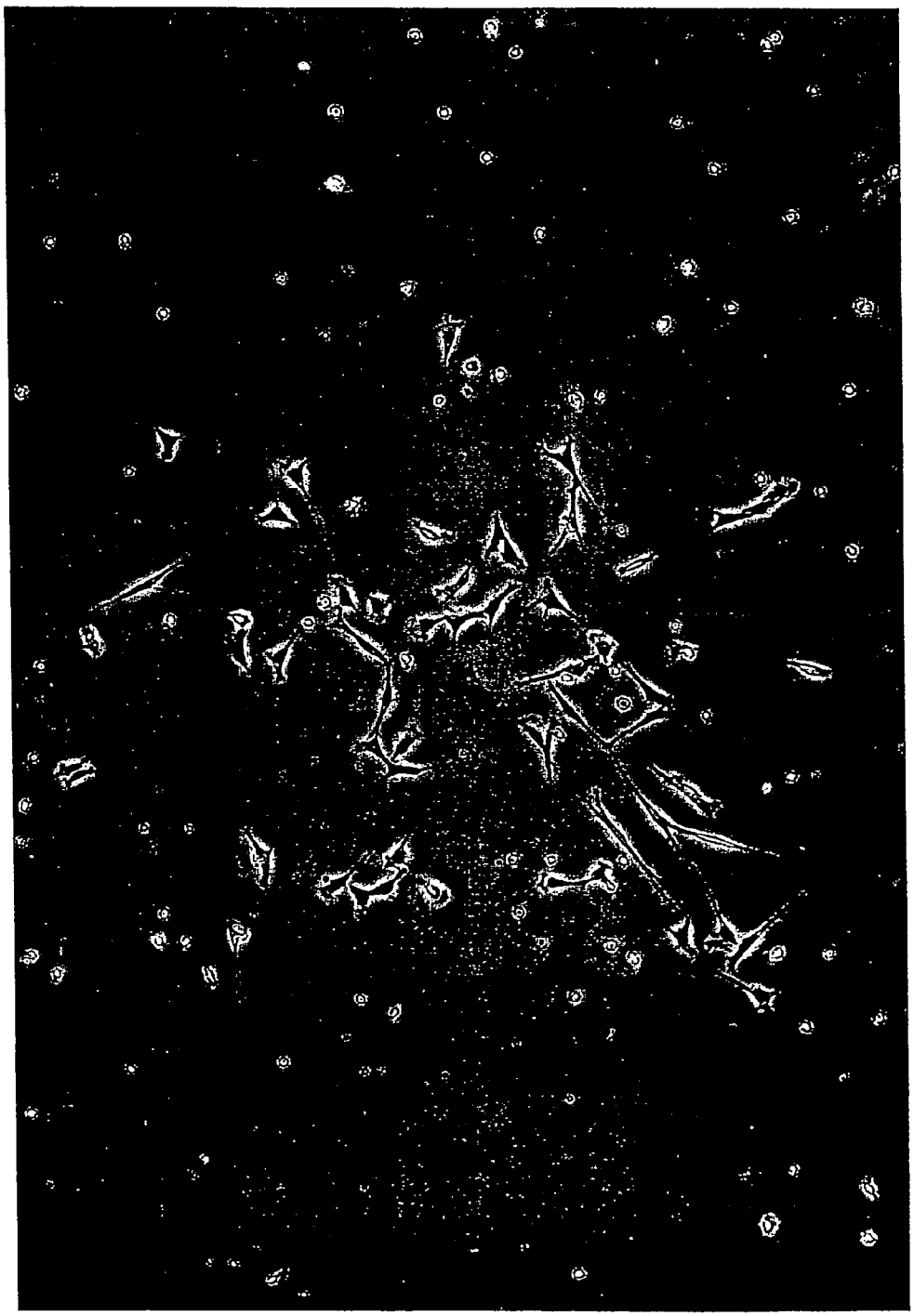

Smith, Results of treatment of bone marrow derived mesenchymal stem cell therapy, Proceedings of the 3rd World Veterinary Orthopaedic Congress, Bologna, 248-249, Sep. 2010.

Bosch et al., Effects of platelet-rich plasma on the quality of repair of mechanically induced core lesions in equine superficial digital flexor tendons: A placebo-controlled experimental study, Journal of Orthopaedic Research, 28:211-217, 2010.

Young et al., Mesenchymal progenitor cell therapy for tendon regeneration, 56th Annual Meeting of the Orthopaedic Research Society, Paper No. 280, 2010.

Dyson, Medical management of superficial digital flexor tendonitis: a comparative study in 219 horses (1992-2000), Equine Veterinary Journal, 36:415-419, 2004.

Reef et al., Initial long-term results of horses with superficial digital flexor tendinitis treated with beta aminoproprionitrile fumarate, Proc. of Annual Convention of the Am. Ass. Equine Practnrs, 43:301-305, 1997.

Hawkins et al., Transection of the accessory ligament of the superficial digital flexor muscle for the treatment of superficial digital flexor tendinitis in Standardbreds: 40 cases (1988-1992), J. Am. Vet. Med. Ass., 206:674-678, 1995.

Hogan et al., Transection of the accessory ligament of the superficial digital flexor tendon for treatment of tendinitis: long-term results in 61 Standardbred racehorses (1985-1992). Equine Veterinary Journal, 27:221-226, 1995.

Smith et al., Effectiveness of bone-marrow-derived mesenchymal progenitor cells for naturally occurring tendinopathy in the horse. Regenerative Medicine 4 (6) Suppl. 2: S25-26, 2009.

Smith, Mesenchymal stem cells: can they help tendon and ligament healing?, Proceedings of the 15th Annual North Carolina Veterinary Conference, Raleigh, North Carolina:1-2, 2010.

Guest et al., Monitoring the fate of autologous and allogeneic mesenchymal progenitor cells injected into the superficial digital flexor tendon of horses: Preliminary study, Equine Veterinary Journal, 40:178-181, 2008.

* cited by examiner (a) Transverse image from level 4 (20cm distal to the accessory carpal bone)
(i) Before implantation
(ii) 10 days after implantation (b) Longitudinal image – 20-24cm distal to the accessory carpal bone
(i) Before implantation
(ii) 10 days after implantation

PHARMACEUTICAL KITS COMPRISING MESENCHYMAL STEM CELLS

This application is the national stage of International (PCT) Patent Application Serial No. GB03/03894 filed Sep. 8, 2003.

The present invention relates to a method of treatment of soft skeletal tissue injury in a patient; in particular, it relates to the treatment of tendon or ligament injuries particularly but not exclusively in competitive or racing mammals such as humans, horses, dogs and camels.

Superficial digital flexor tendon injuries are a common cause of wastage amongst competition horses, associated with a poor success for a return to a previous level of performance and a high incidence of re-injury. Current treatment regimes (reviewed by Dowling et al, 2000) have only marginal effects on the outcome of tendinopathy with the major influence on prognosis being the severity of the initial injury. Recent studies investigating the efficacy of the lysyl oxidase inhibitor, beta-aminoproprionitrile fumarate, demonstrated significant improvements in outcome for moderate to severe superficial digital flexor tendinopathy (Genovese, 1992), although this has not been so favourable in further clinical trials (Reef et al, 1996, 1997) and recent experimental work has demonstrated possible adverse effects of this treatment (Dahlgren et al, 2002). Furthermore, while this treatment prevents collagen cross-links forming too early thereby allowing a controlled exercise regime to improve the functionality of the scar tissue, it does not regenerate tendon tissue. As scar tissue will never be as functional as tendon tissue, a goal of future efficacious treatment is to develop methods of regenerating tendon tissue.

There has been considerable interest recently in the potential therapeutic benefits of mesenchymal stem cells (MSC) for tendon and ligament healing (Woo et al, 1999; Caplan and Bruder, 2001; Hildebrand, et al, 2002). These cells reside in small numbers in all tissues and possess multipotential capabilities of differentiating into a number of different tissues. Recent reports have shown that MSCs can be implanted into tendon and ligament tissue using scaffolds in experimental animals (Young et al, 1998). One source of the MSCs has been bone marrow, and recent reports (Herthel, 2001) have reported considerable success in the use of bone marrow aspirated from the sternebrae and injected direct into the damaged tendon or ligament. In this report, the overall prognosis for a return to full work in 100 horses with suspensory ligament injuries, treated with bone marrow was 84%, while a comparative group of 66 horses treated conservatively had a prognosis of 15%. However, there is no documentation of the numbers of forelimb and hindlimb injuries, nor the region of the suspensory ligament damaged, all of which are known to have very different prognoses (Dyson, 1995, 2000). Furthermore, this technique has many limitations. Injection of large volumes of bone marrow (30-50 ml) would potentially cause considerable disruption of the remaining intact tendon tissue, would include other components of bone marrow such as bone spicules, fat cells, etc deleterious to tendon healing, and only small numbers of MSCs would be expected to be present. Neither the presence of or number of mesenchymal stem cells in this method of treatment have been described or validated Some clinicians have thus doubted the efficacy of this technique as smears of aspirated bone marrow resemble peripheral blood smears. We have also found undesirable mineralisation using the technique.

In a preferred embodiment of the present invention a technique has been developed for the isolation, characterisation, and expansion in vitro of equine MSCs, with re-implantation of large numbers of autologous MSCs into a damaged superficial digital flexor tendon in the horse. MSCs have the potential to differentiate into tenocytes and regenerate tendon matrix after injury.

The invention is not limited to the treatment of horses nor, indeed, to the treatment of the superficial digital flexor tendon or the use of autologous cells, although this is preferred. Rather, it has wider applications as is herein described in detail.

A first aspect of the invention provides a method of treating a natural soft skeletal tissue injury in a patient the method comprising administering to the patient a composition of mesenchymal stem cells in liquid suspension enriched compared to the natural source of said cells or tenocytes derived therefrom.

Soft skeletal tissue includes tendons, ligaments, intervertebral discs, which are associated with spinal pain or injury, and menisci.

Soft skeletal tissue can be injured in various ways, such as by surgical laceration which is a type of percutaneous traumatic injury. Such surgical injuries may be considered to be "unnatural". The injuries for treatment by the present invention are "natural" injuries by which we mean the injury typically occurs subcutaneously, for example by way of being strain induced, which is often an accumulation of damage over a period of time. Thus, natural injuries are clinical injuries and include traumatic injuries that present to the clinician, including accidental lacerations.

Such natural injuries are common in competitive or racing animals, including humans. Natural soft skeletal tissue injuries can readily be diagnosed by the physician or veterinary surgeon using well known techniques such as considering the patient's history, clinical examination, palpation, ultrasound examination, MRI scan and the like.

It is preferred that the injury to be treated is a strain injury.

It is preferred if the soft skeletal tissue that is treated is a tendon or ligament. Particularly preferred tendons or ligaments for treatment by the method of the invention are those that are commonly injured in competitive or racing or athletic animals by strains or an accumulation of damage, such as strain damage.

The patient may be any suitable patient. Typically the patient is a mammal (by which we include humans). Typically, the non-human animal such as a non-human mammal is one of economic importance, such as a racing animal or working or companion animal (such as a dog or cat). Even more typically the animal is a mammal which undergoes competition (ie sporting competition), such as a human, horse, dog (such as whippets, greyhounds, gun dogs, hounds, huskies) or camel.

It is particularly preferred if the patient is a horse which, because of their use in sports (racing, jumping, showing etc), or as work animals, they are particularly susceptible to natural injury to the soft skeletal tissue as defined.

Although in these mammals, any soft skeletal tissue injury can be treated by the method of the invention, particular injuries may more suitably be treated than others. Thus, when the patient is a horse or a camel, it is preferred if the soft skeletal tissue is selected from the group consisting of superficial digital flexor tendon (SDFT), suspensory ligament and deep flexor tendon (in both forelimbs and hindlimbs), accessory ligament of the deep digital flexor tendon (DDFT), menisci, and other ligaments such as the cruciate ligaments. When the patient is a dog, it is preferred if the soft skeletal tissue injury is selected from the group consisting of Achilles tendon, cruciate ligament, meniscus and flexor tendon. When the patient is a human it is preferred if the soft skeletal tissue selected from the group consisting of Achilles tendon, quadriceps tendon, rotator cuff, lateral or medial epichondylitis, cruciate ligament, intervertebral disc and meniscus.

The method is particularly suited to treating flexor tendons rather than extensor tendons. Flexor tendons store energy and accumulated damage that precedes partial or total rupture. Flexor tendons generally do not heal well and injuries thereto have a high morbidity.

It is particularly preferred if the method is used to treat injured tendons or ligaments which store mechanical energy. Thus, treatment of tendinitis (tendonitis), tendinopathy (tendonopathy ie injury to tendon), desmitis (injury to a ligament), bowed tendon, bowed leg and strain injuries is specifically contemplated.

The composition of mesenchymal stem cells may be any suitable composition of such cells provided that the composition is enriched compared to a natural source of said cells. Natural sources of mesenchymal stem cells include bone marrow (eg with and without previous bleeding), peripheral blood (eg with and without enhancement from marrow) and umbilical cord, but also include fat, muscle, blood vessels, periosteum and perichondrium and, in small number, cells into which they differentiate (eg tendon, ligament, cartilage, etc). The composition of cells for use in the invention may be enriched compared to the natural sources by any suitable method, typically involving cell fractionation and concentration methods. Suitable methods are well known in the art and include the Ficoll-Paque methodology described in the Examples. Other suitable methods include concentration of mesenchymal stem cells using antibodies directed to mesenchymal stem cell markers which are immobilised, for example in an affinity chromatography column or to a substratum in a "panning" scheme.

Enrichment can also be achieved by culturing the cells and expanding the cells under conditions which retains their character as a mesenchymal stem cells. Such methods are well known in the art, and one of those is described in detail in the Examples. Mesenchymal stem cells are characterised by multipotency, ie their ability to differentiate into various skeletal and connective tissue cell lines when appropriate biological and/or mechanical signals are present. In particular, mesenchymal stem cells are able to differentiate into cartilage, bone, muscle (such as myotubes), tendon producing cells (tenocytes), fibroblasts and adipocytes (fat producing cells). Suitably, in the enrichment process (including expansion of cells in culture), the presence of (and enrichment of, including expansion in culture) the mesenchymal stem cells can be determined prior to their use in the method of the invention by making the cells differentiate into the different cell lines characteristic for mesenchymal stem cells. Additionally or alternatively, markers (typically cell surface markers) may be useful in the identification of mesenchymal stem cells. In some species, mesenchymal stem cells exhibit the STRO1 marker (but probably not in the horse). Typically, tenocytes produce collagen type I and COMP (see below). The gene "scleraxis" may be a marker for a tenocyte.

Cell types derived from mesenchymal stem cells may be identified using the following markers where + indicates presence of the marker in the cell and − means absence (or trace presence) of the marker in the cell.

| Cell type | Collagen Type I | Collagen Type II | Collagen Type III | COMP | Myosin |
| --- | --- | --- | --- | --- | --- |
| Chondrocyte (cartilage) | − | + | − | + | − |
| Osteoblast (bone) | + | − | − | − | − |
| Tenocyte (tendon, ligament) | + | − | (+) | + | − |
| Fibroblast (fibrous tissue, scar) | + | − | + | − | − |
| Myofibroblast (muscle) | + | − | ? | − | + |
| Adipocyte (fat) | + | − | ? | − | − |

Typically, the enrichment of mesenchymal stem cells in the composition is at least 2-fold over the said cell content in the natural source from which they are enriched. Preferably, the enrichment is at least 3-fold, 4-fold, 5-fold, 10-fold, 20-fold or more preferably at least 30 or 40 or 50 or 100-fold.

Preferably, it is at least 1000-fold or $10^4$-fold or $10^5$ fold.

Typically, the enriched composition contains at least 10% of its cells as mesenchymal stem cells and preferably at least 50% or 60% or 70% or more. It may be advantageous for at least 90% or at least 95% or 99% of the cells in the composition to be mesenchymal stem cells.

It is particularly preferred if the mesenchymal stem cells are derived from bone marrow or umbilical cord blood. It is particularly preferred if the cells are enriched compared to bone marrow, for example using the methods described in the Examples or variants of the method based on the general principles of cell enrichment, expansion (if necessary) and screening. When umbilical cord blood is the source of the mesenchymal stem cells, or tenocytes derived therefrom, it will be appreciated that the cord blood will have been stored for the eventuality that it will be needed for use in the methods of the invention. Thus, it is envisaged that umbilical cord blood will be saved at birth and used, if necessary, in future for the patient.

Although it is envisaged that any composition of mesenchymal stem cells enriched compared to their natural source would be useful, it is preferred if the cells are allogenic (ie from the same species as the patient), as opposed to xenogenic (ie from a different species). If the cells are allogenic, but not autologous, it is preferred if the cells are of a similar tissue type (eg have similar MHC/HLA haplotypes). It is particularly preferred if the cells are autologous (ie are derived from the patient to which they are administered). Such autologous cells have the advantage of being much less prone to rejection compared to other allogenic (or xenogenic) cells. Also, the use of autologous cells avoids any issue of "doping" (eg with "foreign" DNA) which may be of concern. Thus, a particularly preferred method of the invention comprises obtaining mesenchymal stem cells from the patient (for example from the bone marrow), enriching the cells and, if necessary, expanding them in culture, and introducing the so-enriched cells into the patient. It will be appreciated that some of the cells may be saved for use at a later date, and typically such cells are frozen under conditions that retains their viability. It will be appreciated that the cells may be obtained and enriched (expanded if necessary) before any injury to the patient, and kept for immediate administration if and when the patient sustains an injury to the soft skeletal tissue. This procedure means that no time would be lost in starting treatment following injury.

By liquid suspension of cells we include any suitable liquid suspension. For example, the liquid suspension may be a suspension of cells in a medium that contains appropriate biological signals to encourage the differentiation of the mesenchymal stem cells into cell types that are useful to the regeneration of soft skeletal tissue injuries (eg tenocytes in the case of regeneration of tendons), and discourage the differentiation of the cells into cell types that are not useful (eg bone tissue). A suitable liquid suspension is wherein the mesenchymal stem cells are suspended in platelet rich plasma such as descried in the Examples. Suitable liquid suspending media include serum, plasma, platelet rich plasma, bone marrow supernatant, or enriched or conditioned medium. For the avoidance of doubt, the liquid suspension may be one which gels in situ, for example because of the temperature at the injury site of the patient, or because it is mixed with another agent that causes gelling.

Suitable biological signals include molecules that encourage the cells to differentiate in the appropriate way. Such molecules may include growth factors, cytokines which, because of the very high degree of similarity between species need not be autologous or allogenic (eg human growth factors or cytokines may be used in the horse). Suitable growth factors may include TGFβ (preferably isoform 3), IGF 1, IGF 2, PDGF and FGF. It may also be useful to have present in the liquid suspension of cells, other factors that encourage the cells to regenerate as soft skeletal tissue, such as cartilage oligomeric matrix protein (COMP), which may help in soft skeletal tissue formation, but which is often not present in older animals in some species such as the horse. It will be appreciated that although it is preferred if the biological signals are present in the liquid suspension, they may alternatively or additionally be administered separately to the patient, for example at the site of injury. It is particularly preferred that the biological signals or combination thereof used are ones that reduce the possibility of scar formation.

It will be appreciated that the composition of mesenchymal stem cells may be encouraged to differentiate into tenocytes before administration and so the compositions discussed above will also contain tenocytes. Thus, in a particular embodiment, tenocytes derived from the mesenchymal stem cells are administered to the patient. The tenocytes may be in combination with the mesenchymal stem cells and, typically, a composition is used in which the mesenchymal stem cells are committed to differentiate into tenocytes.

Tenocytes may be encouraged to form from mesenchymal stem cells by applying a stretching force to the cells. Typically, this may be done by seeding the cells in a collagen scaffold and pulling (stretching) the scaffold while the cells may be grown in a tissue culture dish with a flexible undersurface which may be stretched as the cells grow.

Cells may be eluted from the collagen scaffold or culture dish surface and used in liquid suspension.

Mesenchymal stem cells do not produce collagen I, whereas tenocytes do produce collagen L so the presence of collagen I is indicative of differentiation of mesenchymal stem cells into tenocytes.

The composition of mesenchymal stem cells, or tenocytes derived therefrom, is administered to the patient in any suitable way. Preferably, the composition is administered directly at the site of injury (or adjacent thereto), and typically such that the mesenchymal stem cells or tenocytes remain at the site of injury. Certain sites of natural soft tissue injury comprise enclosed cavities and it is particularly preferred if the natural soft tissue injury site that is treated is one with such a cavity or a lesion that can readily be closed to form a cavity. When such injuries are treated, the chance of leakage away from the injured site is reduced. It is preferred that the injury treated is an intratendinous partial rupture. In SDFT in horses the lesion along the tendon is commonly in the mid-metacarpal region. In DDFT the lesion is often within the digital sheath. In some cases, the injury is such the damage (eg a tear) opens any cavity, or the injury is at a site where naturally there is no cavity, it may be necessary to introduce packing (for example in the form of a gel matrix), close the cavity or otherwise retain the cells at the site of the injury. Torn tendons or ligaments may be closed surgically to form a cavity into which the liquid suspension of cells may be administered. Alternatively, the composition of mesenchymal stem cells, or tenocytes derived therefrom, may be introduced in the torn tissue and sutured without creation of a specific cavity.

It will be appreciated that the mesenchymal stem cells or tenocytes may be delivered intravenously, or for example into the local blood supply to the site of injury.

It is preferred if the composition of mesenchymal stem cells in liquid suspension or tenocytes is injected into the site of injury. Typically, this is by percutaneous injection, with or without ultrasound to guide the injection to the site of injury (eg within the cavity of a tendon that has been injured). Thus, the needle of a syringe may pass through the skin, straight into the soft skeletal tissue such as a tendon. Suitably, there may be a "stop" on the needle which means that its end is at the desired position within the site of injury for the release of the composition containing the cells. Alternatively, the needle for injection may be guided arthroscopically, which may constitute a minimally invasive way of getting into the soft skeletal tissue such as tendon. Arthroscopic guidance may be particularly useful where the site of injury is intra-articular or intrathecal (ie within a tendon sheath) or intra-articular collagenous structure, cruciate ligament or meniscus.

In one embodiment of the invention, the site of injury is cleansed of damaged tissue and early repair scar tissue that may be starting to form at the site before administration of the composition of mesenchymal stem cells or tenocytes. In this way, it may be possible to prevent or reduce the chances of scar tissue, or other undesirable tissue, formation. This may be done using minimally invasive surgical debridement, or using enzymatic or biophysical methods.

The dose of cells that is administered to the patient may vary by reference to the type and severity of the injury, and may be determined by the physician or veterinary surgeon. Typically, the liquid suspension is administered in about 0.1 ml aliquots (or 0.2 ml or 0.3 ml or 0.4 ml but typically no more than 0.5 ml aliquots) at the site of injury. Typically, an aliquot, such as a 0.1 ml aliquot, contains from about 50 000 to 500 000 mesenchymal stem cells or tenocytes.

The size and/or number of aliquots may vary depending on the nature and extent of the injury. The volume of the lesion (site of injury) may be accurately determined by ultrasonography. The volume of the lesion can generally be determined from the ultrasound pictures alone. Typically, when the injury is at a site which has a cavity (or can be made to form a cavity by packing as described above), the cavity is filled with the liquid suspension of cells).

It is preferred that the treatment regimens of the invention starts as soon as possible after injury; however, it may be advantageous to allow the blood to clot and start to form early granulation tissue to induce or enhance the blood supply. Desirably, treatment starts within 24 hours to 4 weeks, typically within 48 hours to 7 days.

In a preferred embodiment of the invention, the regeneration of the soft skeletal tissue at the site of injury is monitored by ultrasonography including the measurement of, cross-sectional areas (eg by ultrasonography). It is also particularly preferred that following the treatment the patient is subjected to a rehabilitation procedure involving exercise of the injured site. Typically, if the cross-sectional area of the damaged tissue (such as tendon or ligament) increases by more than 10% at any level, exercise is reduced, whereas if it remains constant or decreases, exercise is gradually increased. Suitable rehabilitation (eg exercise) regimens can readily be devised by the physician or veterinary surgeon having regard to the nature of the injury, the treatment thereof and the progress made by the patient in regenerating suitable soft skeletal tissue at the site of injury. A suitable rehabilitation regimen is shown for the treatment of SDFT in the horse.

A further aspect of the invention provides the use of a composition of mesenchymal stem cells in liquid suspension enriched compared to the natural source of said cells or tenocytes derived therefrom in the manufacture of a medicament for treating a natural soft skeletal tissue injury in a patient.

A further aspect of the invention provides a kit of parts comprising (1) a composition of mesenchymal stem cells in liquid suspension enriched compared to the natural source of said cells or tenocytes derived therefrom, (2) means for delivering the liquid suspension of stem cells to a site of natural soft skeletal tissue injury in a patient and (3) means for determining that the means for delivering locate to the site of injury.

A further aspect of the invention provides a kit of parts comprising (1) a stored sample of umbilical cord blood, (2) details of the individual it was obtained from, and (3) instructions for preparing a composition of mesenchymal stem cells in liquid suspension enriched compared to the blood, or tenocytes derived therefrom.

The invention will now be described in more detail by reference to the following non-limiting Figures and Examples.

FIG. 1 shows equine mesenchymal stem cells adhering to plastic after semi-purification from bone marrow by Ficoll centrifugation.

Figure 2:
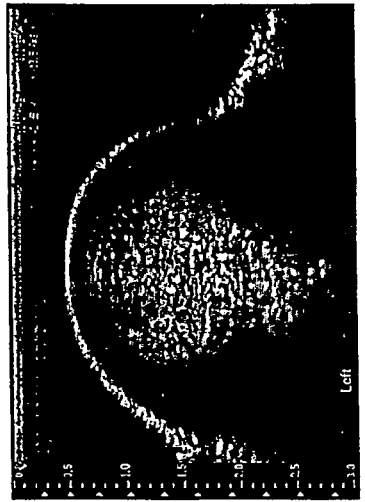
Figure 2:
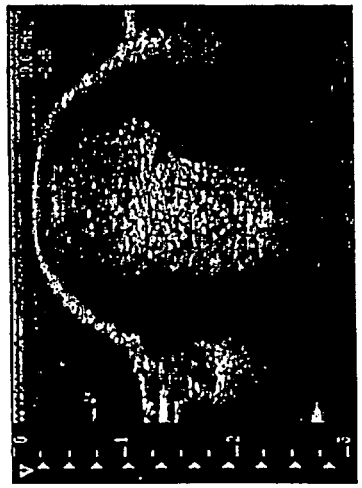
Figure 2:
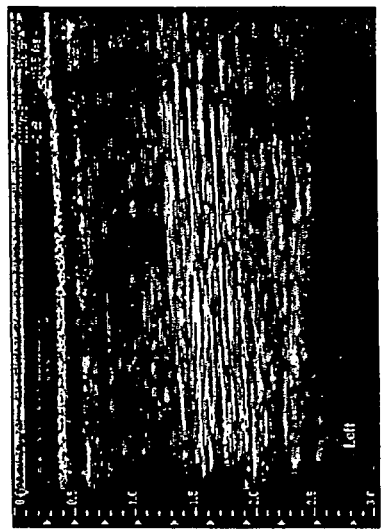
Figure 2:
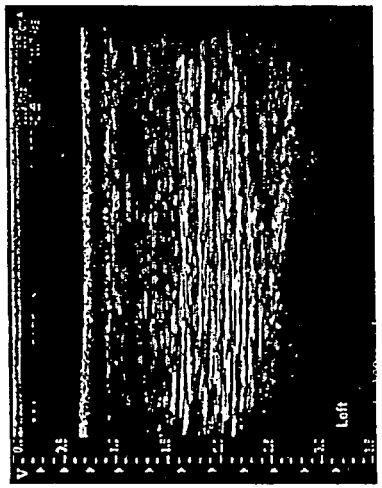
Figure 3A:
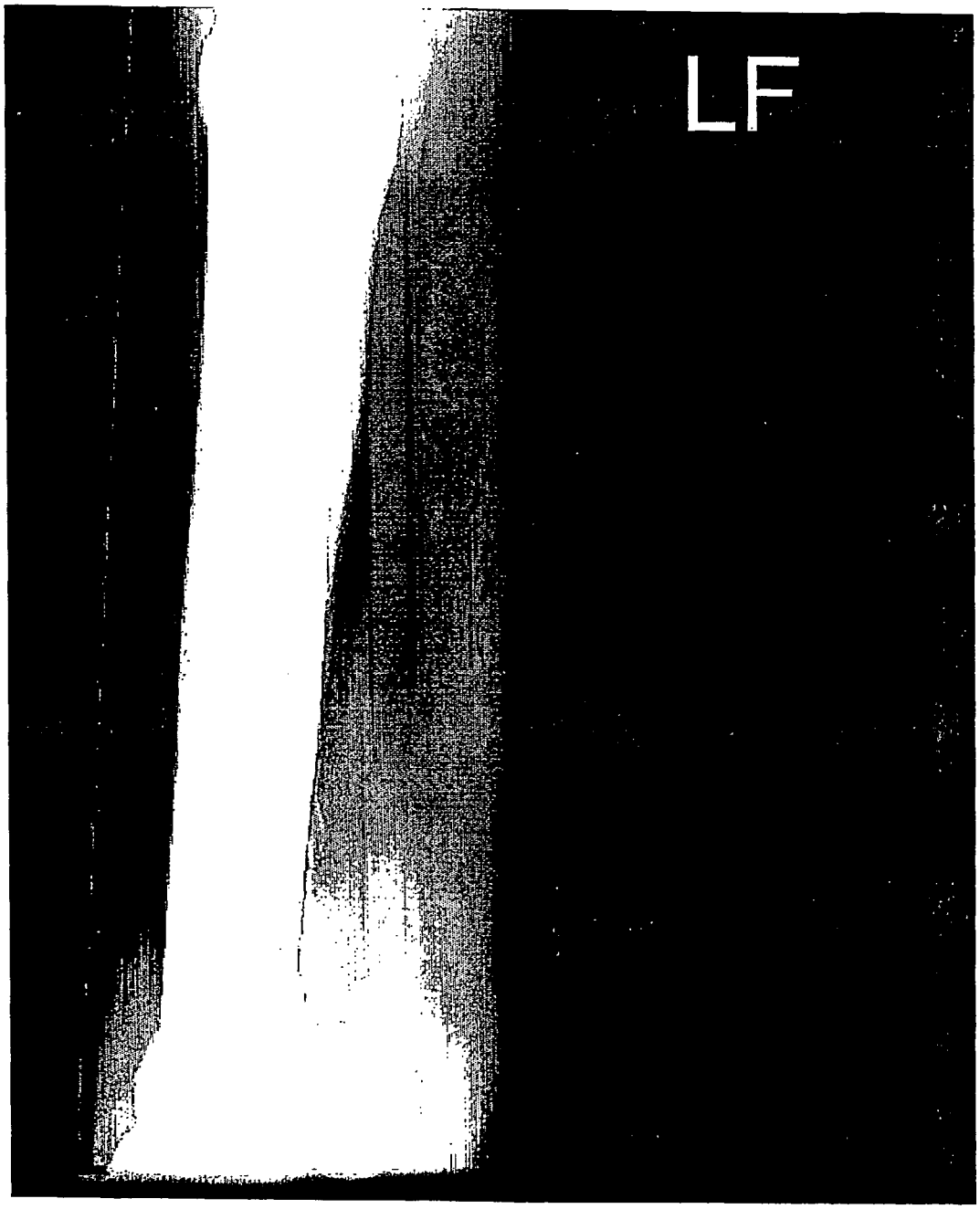
Figure 3B:
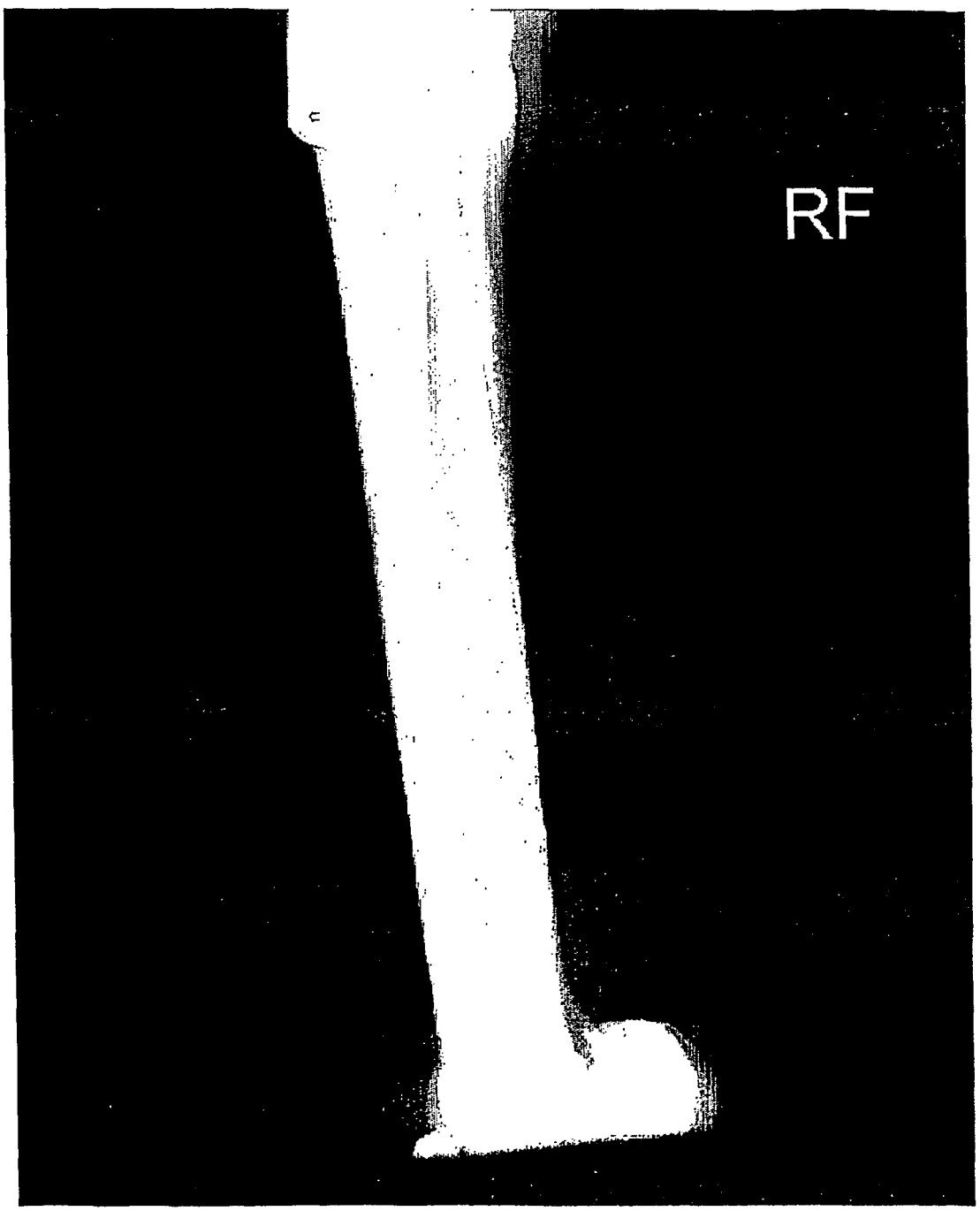
Figure 3C:
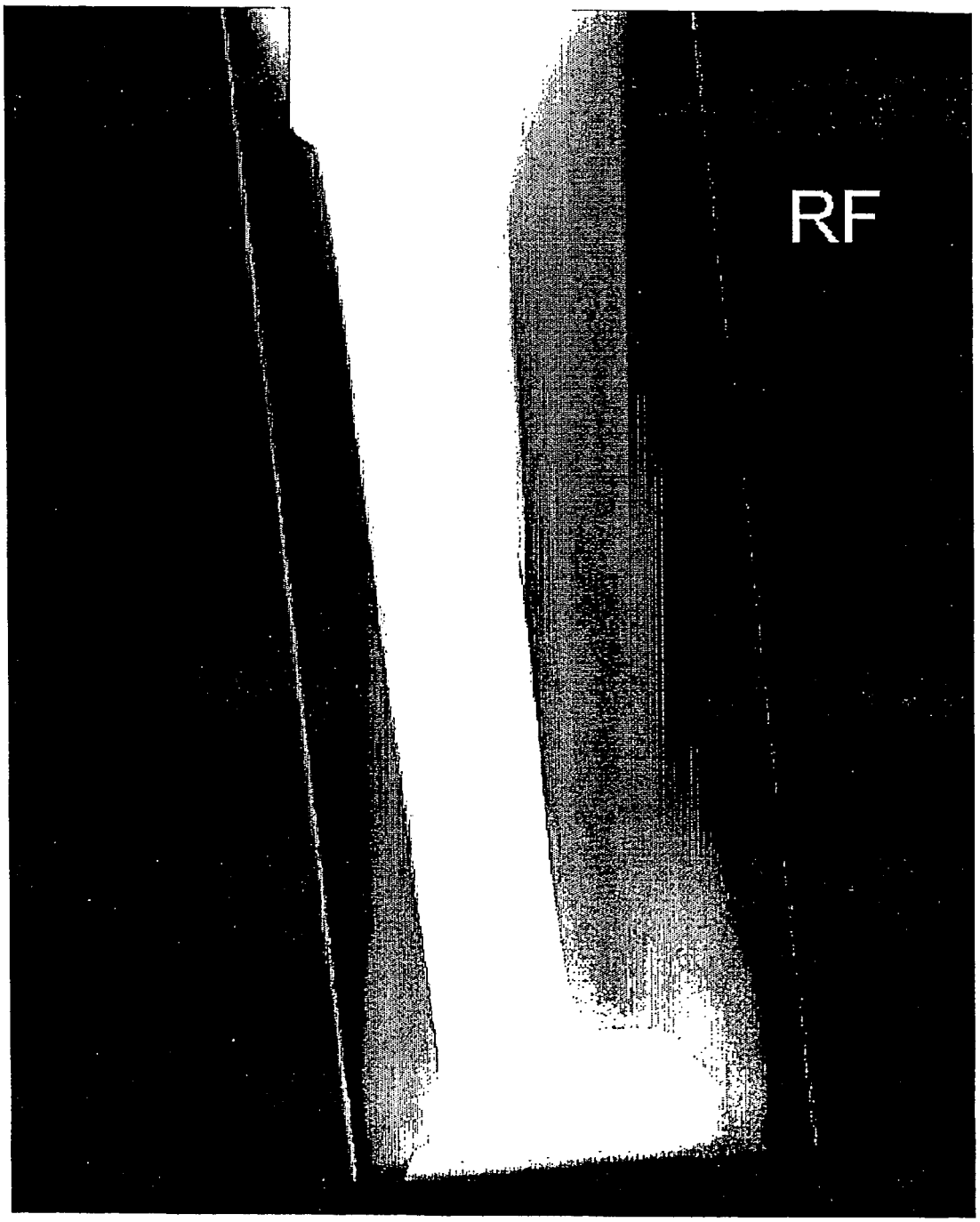
Figure 3D:
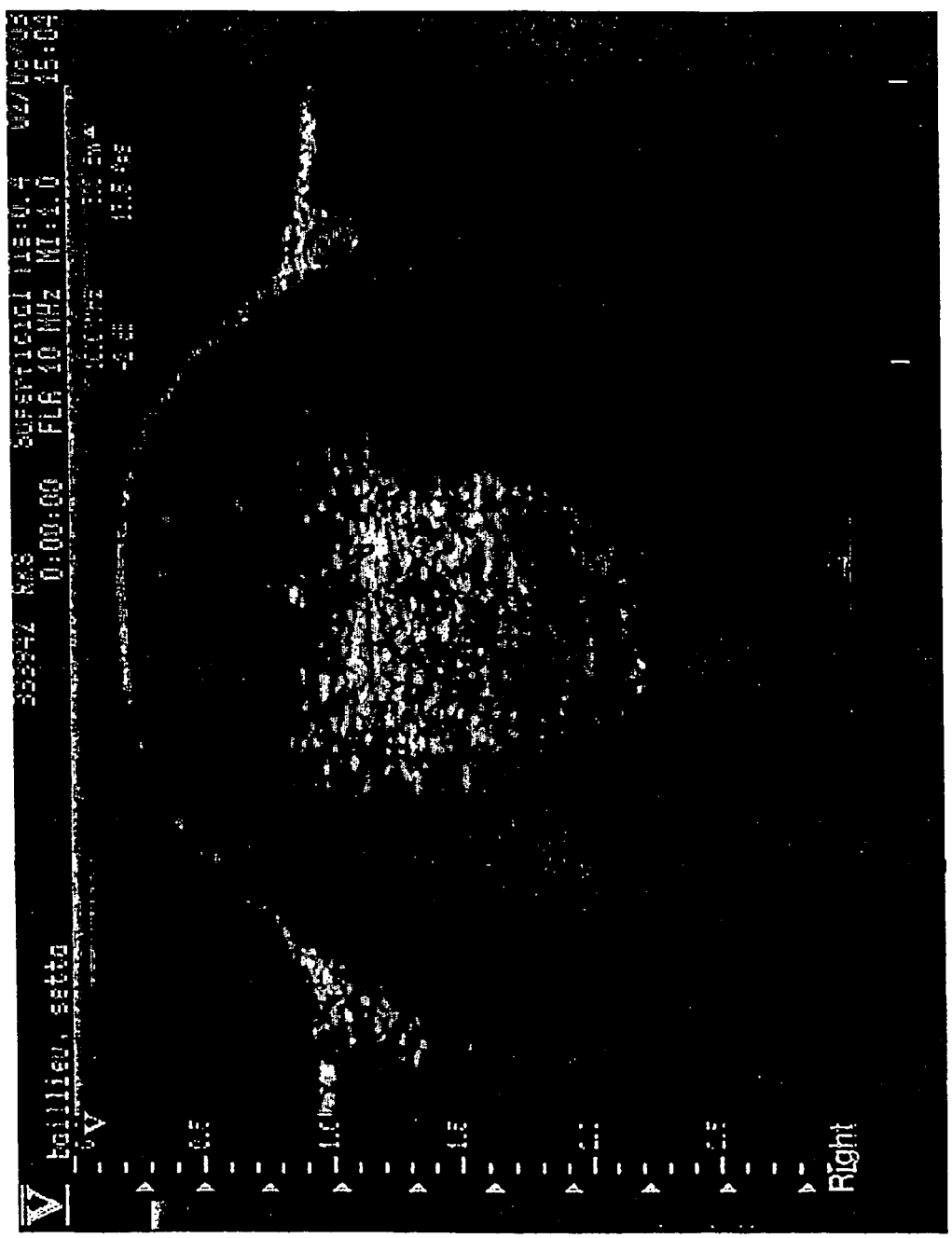
Figure 3E:
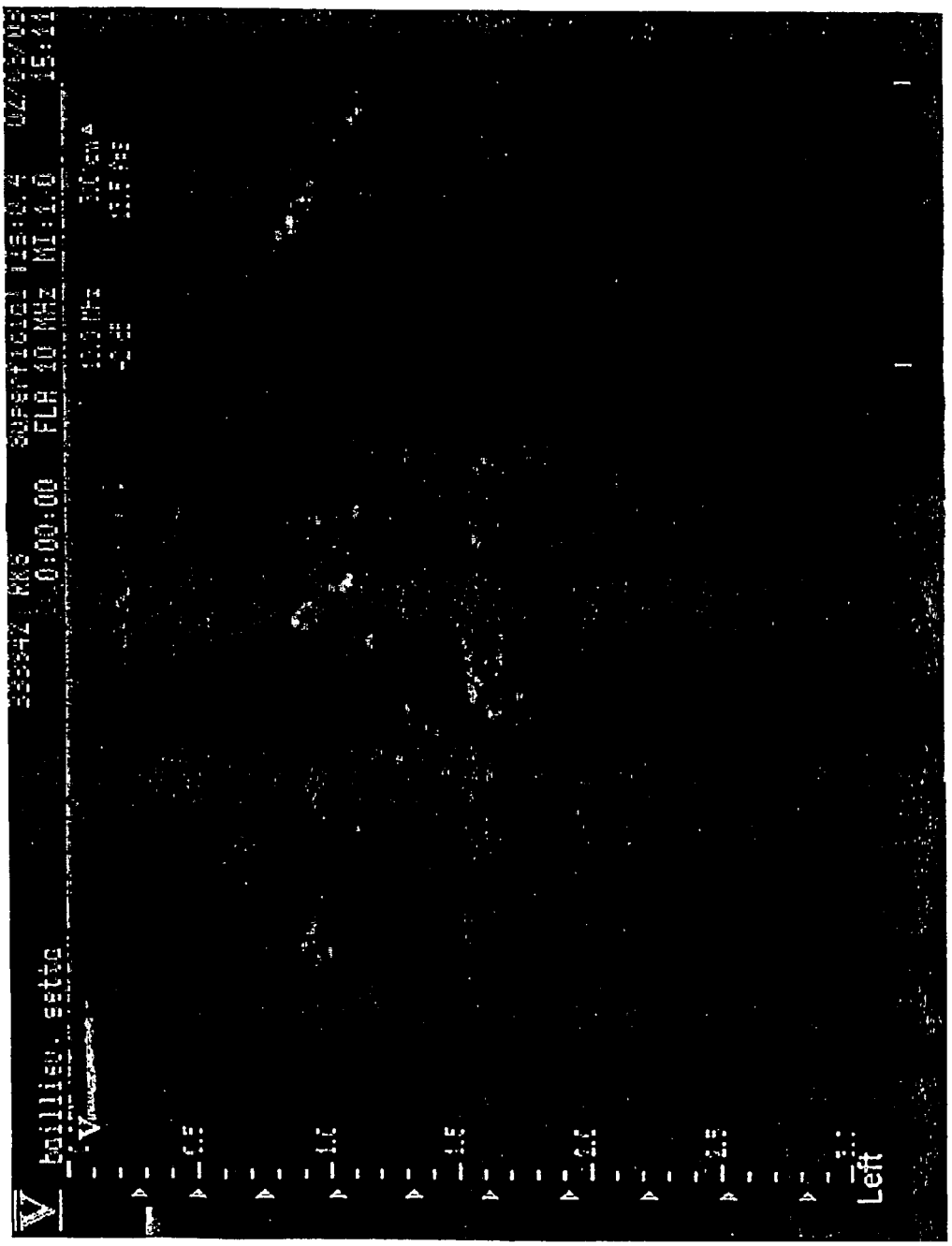
Figure 3F:
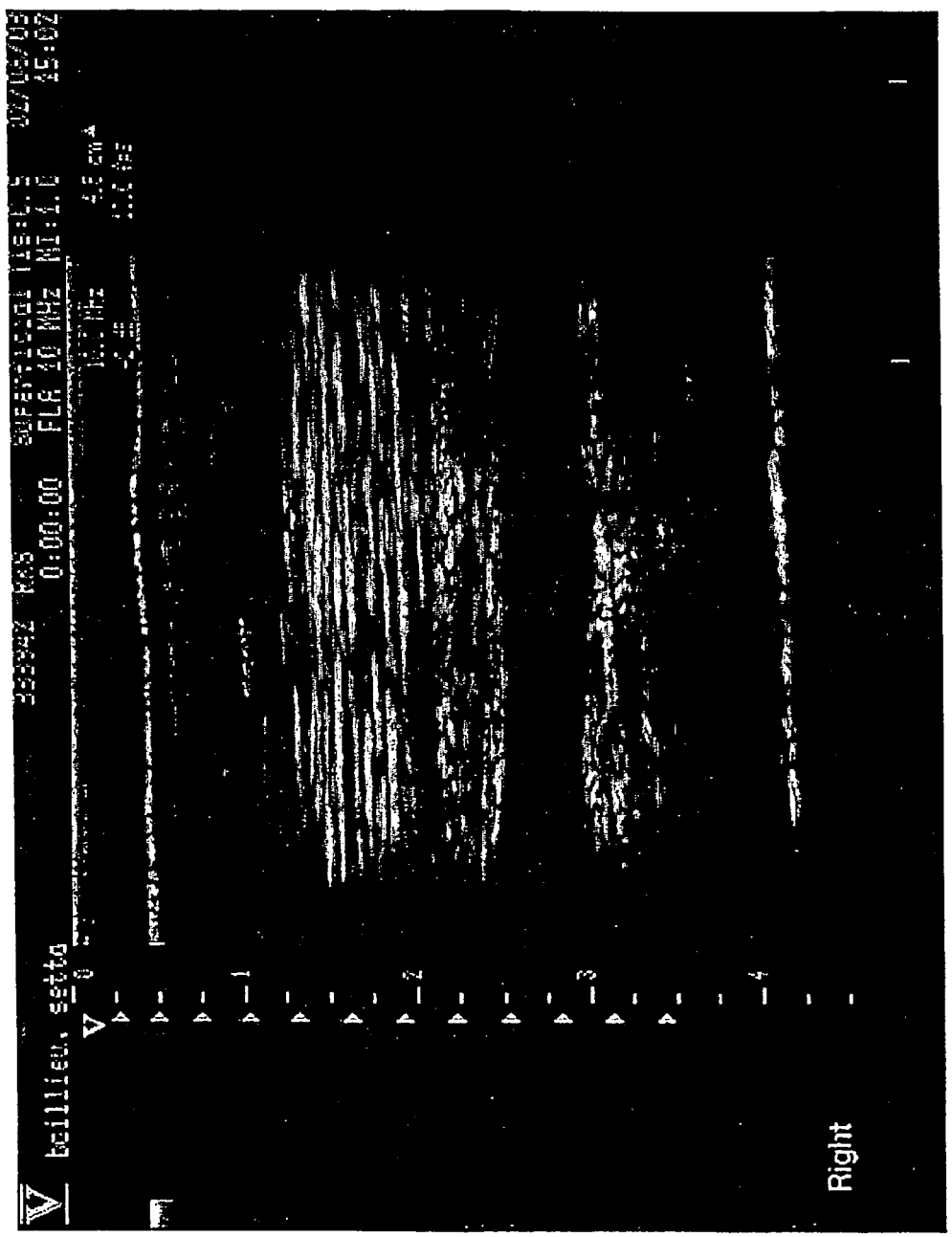
Figure 3G:
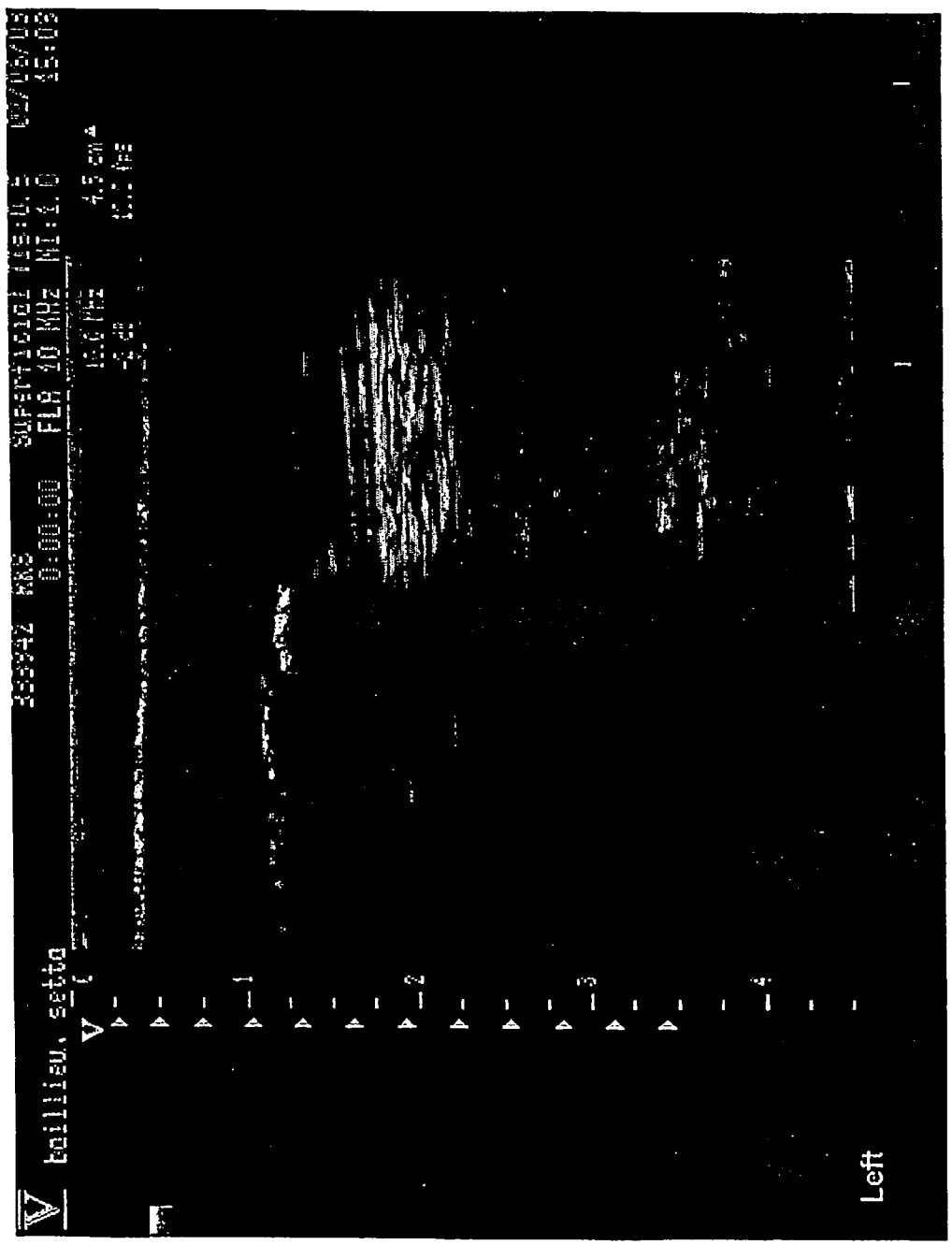

FIG. 2 shows ultrasonographs of the superficial digital flexor tendon of an 11 year old polo pony with a superficial digital flexor tendonitis of 5 weeks duration prior to stem cell implantation and 10 days after stem cell implantation. The lesion occupies the central 45% of the tendon and is filled with granulation/young fibrous tissue. There has been no significant disruption to the healing tendon by the implantation procedure.

(a) Transverse image from level 4 (20 cm distal to the accessory carpal bone).
  (i) Before implantation.
  (ii) 10 days after implantation.
(b) Longitudinal image—20-24 cm distal to the accessory carpal bone.
  (i) Before implantation.
  (ii) 10 days after implantation.

FIG. 3 shows scans following treatment, as described in Example 4.

EXAMPLE 1

Isolation of Equine Mesenchymal Stem Cells from Bone Marrow and their Implantation into the Superficial Digital Flexor Tendon as a Potential Novel Treatment for Superficial Digital Flexor Tendinopathy Materials and Methods
Case Details Autologous MSCs were re-implanted after expansion in vitro into a damaged superficial digital flexor tendon of an 11 year old polo pony that had suffered a strain-induced injury of its superficial digital flexor tendon 5 weeks previously.
Bone Marrow Aspiration:

After sedation (with 10 µg/kg detomidine hydrochloride[1] (Domosedan, Pfizer Animal Health, Ramsgate, Kent) and 20 µg/kg butorphanol (Torbugesic, Fort Dodge Animal Health, Southampton, UK)), an area 5 cm×20 cm over the sternum was prepared by clipping and scrubbing. After aseptic preparation, the intersternebral spaces, easily identified by diagnostic ultrasonography, were marked on the skin using a sterile marker pen. Local anaesthetic solution (2 ml; mepivicaine (Intra-Epicaine, Arnolds, Shrewsbury, UK)) was infiltrated subcutaneously over the midpoint in the sagittal plane of two adjacent sternebrae. A stab incision with a number 11 scalpel was made through the skin. A Jamshidi biopsy needle (11 G, 4 inch) was introduced approximately 4-6 cm until it contacted the sternebra. It was then pushed a further 34 cm into the sternebra and then 1.8 ml aliquots of bone marrow from each of two sternebrae was aspirated into 2 ml syringes, pre-loaded with 1000 iu heparin (Heparin (Multiparin, CP Pharmaceuticals, Wrexham, UK); 5000 iu/ml). Five aliquots were taken in the first series of aspirates to quantify MSCs cell numbers and thereafter 2 aliquots were taken for preparation of MSCs for re-implantation. The 1.8 ml marrow aspirates were gently oscillated and then transferred into sterile 5 ml tubes and placed on ice for immediate transfer to the laboratory.

Mesenchymal Stem Cell Isolation and in vitro Culture and Expansion:

The MSCs were separated using a technique similar to that described for the isolation of MSCs in other species (Rickard et al, 1996). In brief, the initial 2 ml of a bone marrow aspirate was layered gently onto 4 ml Ficoll (Ficoll Paque PLUS, Amersham Pharmacia Biotech UK Ltd, Little Chalfont, UK). This layered mixture was then centrifuged at 1510 rpm (400 g) for 30 minutes so that a straw coloured buffy layer formed in between the plasma and Ficoll erythrocyte residue. This buffy layer was recovered and washed by adding 10 ml Dulbecco's Modified Eagles Medium (DMEM, Sigma Aldrich, Poole, UK; 4500 mg/L glucose, L-glutamine and sodium pyruvate with 10% foetal calf serum, penicillin 50 iu/ml, and streptomycin 50 µg/ml). The sample was spun at 2000 rpm (702 g) for 10 minutes to remove heparin and Ficoll. The supernatant was discarded and the cell pellet resuspended in 12 ml DMEM. This cell suspension was then added to T75 flasks.

The primary seeded cells were allowed to adhere to the flask for two days before changing the medium, and thereafter the medium was changed every two days for 14-16 days when colony-forming units were visible. These cells were passaged before confluency by trypsinisation into T175 flasks and then expanded for a further 5-9 days until confluent.

Cells were removed from the flasks using trypsin digestion and centrifuged at 2000 rpm (702 g) for 10 minutes to pellet the cells. The medium supernatant was discarded and the cell pellet was resuspended in 1 ml of fresh DMEM without serum. A 20 µl aliquot was aspirated and counted in a haemocytometer to give the cell count per millilitre.

Quantification of MSCs in Sequential Aliquots of Bone Marrow:

To quantify the yield of MSCs from equine bone marrow, sequential 1.8 ml aliquots of bone marrow from three different horses (including the horse in which re-implantation was performed) were cultured separately. Cell numbers were determined after the colony-forming units were established, and at confluence after first passage.

Re-Implantation of MSCs into Superficial Digital Flexor Tendinopathy:

$6.4 \times 10^5$ cells (to give 40-50,000 cells/0.1 ml injected) were re-pelleted by centrifugation and then resuspended in 1.5 ml of platelet-rich plasma (PRP). The PRP was prepared from freshly obtained blood from the same horse by collecting 10 ml blood into sterile blood tubes containing 500 iu/ml heparin and centrifugation at 1620 g for 12 minutes. The top 2.5 ml of plasma was discarded and then 2.5 ml of PRP aspirated. This technique has been found to yield PRP with more than three times the number of platelets than normal plasma.

This 1.5 ml cell suspension was then injected into the damaged superficial digital flexor tendon of the same horse from which the cells were originally derived. The injection was performed in a sterile fashion under sedation and perineural analgesia at the proximal metacarpal site, in 15×0.1 ml (approximately 43,000 cells/0.1 ml) injections administered using a 23 G, 1 inch needle along the length of the lesion from the palmar and medial aspects of the tendon while monitored ultrasonographically. The limb was then bandaged with a standard three-layered modified Robert Jones bandage.

Results

This protocol resulted in the generation of colony-forming units characteristic of MSCs in other species (FIG. 1).

Quantification of MSCs in Sequential Aliquots of Bone Marrow:

The number of cells recovered before and after passage is shown in Table 1

TABLE 1

Quantification of MSCs from sequential bone marrow aliquots after in vitro culture.

| Sample | Cell numbers from colony-forming units (subconfluent) (×10$^5$) | | | Passage 1 (confluence) (×10$^5$) | | |
|---|---|---|---|---|---|---|
| Horse no. | 1 | 2 | 3* | 1 | 2 | 3* |
| Days culture | 19 | 16 | 14 | 5 | 5 | 9 |
| Peripheral blood (control) | — | 0 | — | — | — | — |
| Aliquot 1 | 31 (aliquots | 9.0 | — | 78 | 61.4 | — |
| Aliquot 2 | 1 + 2 combined) | 21.4 | — | — | 57.8 | — |
| Aliquot 3 | — | 2.2 | — | — | 44.6 | 45.2$^+$ |
| Aliquot 4 | 7.2 (aliquots | 16.8 | — | 44.8 | 73 | — |
| Aliquot 5 | 4 + 5 combined) | 21.8 | — | — | 66 | — |
| AVERAGE | 12.2 (n = 9) | | | 47.1 (n = 10) | | |

*= Horse used for implantation
$^+$= Sample used for implantation

These cell numbers reflect the relative number of MSCs isolated in aliquots from the same horse as all samples were passaged at the same time. Approximately a million cells were obtained after initial culture for 14-16 days. In addition, it shows that passage will expand the cell numbers by a factor of between 2 and 20 times. No MSCs were cultured from a control sample of peripheral blood.

Injury Characteristics

There was a central hypoechoic region in the superficial digital flexor tendon which occupied 45% of the cross-sectional area of the tendon at the maximum injury zone and extended from the mid to distal metacarpal region (levels 3-5 (Smith et al, 1994); 16-26 cm distal to the accessory carpal bone). The cross-sectional area of the tendon at the maximum injury zone was 64% larger than the contralateral tendon. The central lesion had already begun to fill with echogenic granulation/fibrous tissue (FIG. 2).

Reimplantation of MSCs:

Accurate placement of the MSCs into the central tendon lesion was identified clearly from the air bubbles introduced at the time of injection. The injected cell/plasma mixture was observed to extend proximodistally to the limits of the lesion.

There was no observable swelling of the limb after the procedure. At re-examination, 10 days after implantation, there was no lameness at the walk and there was no increased thickening in the region of the superficial digital flexor tendon, although there was mild pain on digital pressure. Repeat ultrasonography showed no change in the substance of the tendon (FIG. 2). Cross-sectional area measurements from all seven levels showed minimal change from the re-implantation (average percentage change for all levels, 0.46% (decrease); maximum change at any one level, 9% (decrease)). There was thus no disruption to the tendon substance.

Discussion

This novel technique provides a method for the re-implantation of large numbers of autologous MSCs, which have been expanded in numbers in vitro, into the damaged tendon of the same horse. These cells have the potential to produce actual tendon matrix rather than poorly functional scar tissue, as occurs with conventionally managed superficial digital flexor tendinopathy. Equine superficial digital flexor tendinopathy, with its frequent centrally-positioned damage and surrounded either by relatively intact tendon tissue or thick paratendon (which invariably remains intact after even the most severe train-induced tendon injuries), in a tendon of sufficient size to make accurate intra-tendinous injection practical, lends itself perfectly as an enclosed vessel in which to implant MSCs. While the implantation of MSCs into other forms of damaged tendons and ligaments (eg eccentric lesions) may also prove to be beneficial, accurate placement, retention of cells, and minimising iatrogenic trauma caused by the injection process are more problematical, but may still be done, for example by using suspensions which gel in situ.

There was a larger variation in the cell numbers before than after passage because the cell numbers measured before passage were at sub-confluence and related to the number of colony-forming units on the plate derived from individual MSCs. Cell numbers at confluence after passage would be expected to be more constant because the cells expand until they cover the whole of the flask surface. Passage will therefore often be necessary to expand the numbers sufficiently.

An attempt was made to introduce approximately 50,000 cells/0.1 ml (approximately 500,000 cells in total). In view of the rapid expansion of cells in vitro after passage, it was expected that this number of cells would be sufficient to populate the central lesion in the tendon. Certainly, in vitro expansion of MSCs enables the autologous implantation of considerably larger numbers of MSCs than that available endogenously or delivered by direct injection of bone marrow, and avoids the potential adverse effects of other components of a bone marrow aspirate. In addition, storage of surplus cells frozen provides an additional source of MSCs if required subsequently.

Sufficient time had been allowed in this horse for adequate angiogenesis and granulation tissue to form which would be more likely to support MSCs than an earlier haemorrhagic lesion. Abundant growth factors are present in early healing tendon tissue (Cauvin, 2001) and the expanded MSCs were delivered in a platelet-rich plasma to augment this growth factor milieu.

This study has demonstrated that the first few millilitres of a bone marrow aspirate from the sternum can yield substantial numbers of MSCs after expansion in culture (in the order of 10$^6$ cells from 1.8 ml of bone marrow). The technique of equine MSC recovery from bone marrow, ex vivo culture and expansion, and re-implantation is both rational and feasible.

Since commencement of the study, we have treated six cases which have done well. Two horses with obvious hypoechoic defects ("black holes") in the tendon at the time of implantation showed rapid filling in of the defects. The others, which were more chronic, and hence already largely filled in at the time of implantation, showed less change.

EXAMPLE 2

Further Detailed Protocol for Treating Superficial Digital Flexor Tendon or Suspensory Ligament Injury Criteria for Inclusion of Cases:

Superficial digital flexor tendon or suspensory ligament injury of the palmar aspect of the metacarpus which does not involve a tendon sheath. Only lesions with defined core lesions will be included and the current injury should be more than 3 weeks and less than 3 months in duration.

Protocol:
1) Baseline clinical examination to include full ultrasonographic examination and blood sample (for preparation of platelet-rich plasma and markers studies).
2) Cross-sectional areas of the damaged tendon to be calculated including tendon and lesion cross-sectional area for all seven transverse levels in the metacarpal region to give a percentage involvement of the lesion (severity).
3) After sedation (alpha 2 agonist and butorphanol), clipping and scrubbing over the sternum, individual sternebrae will be identified using diagnostic ultrasound and the inter-sternebral space marked on the skin with a sterile marker.
4) Local infiltration of local anaesthetic will be placed over the site for marrow aspiration (in centre of two adjacent sternebrae). A stab incision is made through the skin using a No 11 scalpel. A Jamshidi biopsy needle is introduced until it hits to the sternebra. It is pushed a further 3-4 cm into the sternebra and then 2×2 ml aliquots of bone marrow from each of two sternebrae is aspirated into 2 ml syringes, pre-loaded with 500 iu (0.2 ml of 5000 iu/ml in each syringe) heparin.
5) After the aliquots have been obtained, a further 20 ml is withdrawn from one sternebra into a syringe pre-loaded with the same concentration of heparin (2 ml in 20 ml syringe). The bone marrow aspirate is then spun down at 2000 rpm for 20 mins and the supernatant collected, transferred to sterile 20 ml tubes, and frozen at −20° C.
6) 2 ml aliquots transferred into sterile 5 ml tubes.
7) Immediate transfer to Stanmore on ice.
8) Aliquots used for recovery and culturing of MSCs (see attached protocol on page 4).
9) Expansion of MSCs over approximately 1-2 week period until colonies of MSCs formed on plastic. Cella passaged and expanded further (for ~5 days until confluent) when there are approximately $7 \times 10^6$ cells/ml.
10) Cells removed from the flasks and divided into 3 aliquots.
11) Spun down in sterile tubes (1000 rpm for 10 minutes) to pellet the cells.
12) Aliquot 1—used to characterize cells (ie ensure they are MSCs).
Aliquot 2—cells frozen down in DMSO (for potential future use).
Aliquot 3—prepared for injection.
13) Supernatant removed.
14) Cell pellet (approximately $7 \times 10^6$ cells) washed with fresh DMEMs without serum.
15) Spun down in sterile tubes (1000 rpm for 10 minutes) to pellet the cells.
16) Cells resuspended in 2 ml platelet-rich plasma (PRP) (or marrow supernatant), previously thawed, derived from the same horse.
17) Cells injected into the damaged tendon in a sterile fashion under sedation and perineural analgesia using multiple needle stabs (23 G, 1 inch needle—10 injections of 0.1 ml along the length of the lesion.
18) Limb bandaged with a standard modified Robert Jones bandage.
19) Tendons scanned at 3 days after injection and then the horse discharged from the hospital.
20) Tendons scanned at 3 days after injection and then the horse discharged from the hospital.
21) Horse is box-rested for 1 week and then given walking in hand exercise for a further 3 weeks before repeat ultrasound examination.
22) Repeat ultrasound examinations and blood samples at monthly intervals while following the controlled exercise programme shown below:

| GUIDELINES FOR CONTROLLED EXERCISE PROGRAMME | | |
|---|---|---|
| Level | Minimum weeks after injury | Duration and nature of exercise |
| 1 | 0–8 | 30 minutes walking daily building this up to 45 minutes |
| 2 | 9–32 | walking + 5 minutes trotting building up to 30 minutes |
|  | 9–12 | 40 minutes walking and 5 minutes trotting daily |
|  | 13–16 | 35 minutes walking and 10 minutes trotting daily |
|  | 17–24 | 30 minutes walking and 15 minutes trotting daily |
|  | 25–28 | 25 minutes walking and 20 minutes trotting daily |
|  | 29–32 | 15 minutes walking and 30 minutes trotting daily |
| 3 | 33–52 | Walk and trot with restricted canter work |
|  | 33–36 | 45 minutes exercise daily with slow canter up to 1 mile twice weekly |
|  | 37–40 | 45 minutes exercise daily with slow canter up to 1.5 mile twice weekly |
|  | 41–44 | 45 minutes exercise daily with one 3 furlong gallop three times a week |
|  | 45–48 | 45 minutes exercise daily with one 6 furlong gallop three times a week |
|  | 49–52 | Increase exercise level gradually to full race/competition training |
| 4 | From 52 weeks | Full race/competition training |

23) Compare results with an age-matched group of horses with similar lesions managed conservatively with the above exercise programme alone.

Outcome Measures:
Ultrasonographic progression
Marker levels
Athletic outcome
If euthanased, tendon recovered for mechanical and matrix analyses.

Protocol for Equine Mesenchymal Stem Cell Isolation from Bone Marrow

Materials

| | |
|---|---|
| Ficoll | Marrow |
| 5 ml syringe | pipette 12 ml ×3 |
| Green syringe needle | pipettor |
| Universal | waste pot |
| Transfer pipette ×2 | |

Ficoll Gradient
1. Invert bottle of Ficoll to mix, snap off polypropylene cap, insert syringe through septum injecting air to equalise pressure. Invert bottle and withdraw 3 ml liquid.
2. Gently lay 4 ml bone marrow onto 30 ml Ficoll. The two layers are best achieved by holding the universal straight up and dispensing the marrow slowly down the side of the universal.
3. Centrifuge at 1510 rpm for 30 minutes (program 5 centrifuge in room 2 stops slowly and does not disturb layers) so that a straw coloured buffy layer forms in between the plasma and Ficoll erythrocyte residue.
4. Remove buffy layer to a fresh universal using a transfer pipette. Only mononuclear sells should be left in suspension.

Seeding Flasks
Materials
DMEM: 500 ml 4500 mg/L glucose, L-glutamine and sodium pyruvate
Foetal calf serum 10%, 50 ml
Penicillin 50 u/ml and Streptomycin 50 µg/ml
T75×2/T25×2
Waste pot
23 needle
5 ml syringe
12 ml pipettes×3

5. Wash the buffy layer by resuspending the cells in 10 ml DMEM. Spin at 1500 rpm for 10 minutes to remove heparin and Ficoll.
6. Remove supernatant. Stem cells should be in the pellet.
7. Resuspend pellet in 2 ml DMEM using a 23 gauge syringe needle to give a single cell suspension.
8. Divide cells into two T75 flasks. T25s can be used if there was only a small volume of aspirate taken.

Washing Cells
9. Allow primary seeded cells to adhere to the flask for two days before changing the medium. (If setting up cells on Thursday, leave over the weekend.)
10. Change medium every two days.

Observations
The flasks may appear cloudy. This is because there are erythrocytes in the suspension that will be washed off in subsequent DMEM washes.
Stem cells can initially be observed as round shiny objects that have adhered to the flask unlike the surrounding cells in suspension.
CFU-Fs should be seen after two weeks in culture.
NB 100-500 Human MSCs result from 50-100 million cells introduced into culture (Hayensworth S. E. et al).
Horse stem cells Aim
Isolation and expansion of horse MSCs with a view to reinjecting the cells into the tendon.

Hypothesis
The number of cells in the initial 4 ml of aspirate extracted from horse marrow will yield a larger number of cells compared to the final 4 ml.
1. Marrow aspirate was taken from the horse sternum in the following aliquots (500 u/ml of heparin was used):
   1) Sample 1: 1-2 ml
   2) Sample 2: 3-4 ml
   3) Sample: 5-6 ml (given to horse)
   4) Sample 3: 7-8 ml
   5) Sample 4: 9-10 ml
2. Sample 1 and 2 were combined to give the first 4 ml of a 10 ml sample. Sample 3 and 4 were combined to give the final 4 ml of the 10 ml sample. They were named:
   HS1 A: Sample 1+2
   HS1 B: Sample 3+4
3. The technique for isolating stem cells from bone marrow outlined above was followed. Cells were passaged at into 2×T75 flasks and were left in culture for 19 days.
4. Cell were counted and passaged into 2×T175 flasks.
   Cell count:
   HSA1 P0 T75 ... $3.1 \times 10^6$ cells/ml
   HSB1 P0 T75 ... $7.2 \times 10^5$ cells/ml
5. Cells were cultured for a 5 days until they reached confluency. Cells were counted at P1 and frozen down in DMSO.
   Cell count:
   HSA 1 P1 T175 ... $7.8 \times 10^6$ cells/ml
   HSB 1 P1 T175 ... $4.48 \times 10^6$ cells/ml Results
Cell count at P0:
HSA 1 P0 T75 ... $3.1 \times 10^6$ cells/ml
HSB 1 P0 T75 ... $7.2 \times 10^5$ cells/ml
Cell count at P1:
HSA 1 P1 T175 ... $7.8 \times 10^6$ cells/ml
HSA 1 P1 T175 ... $4.48 \times 10^6$ cells/ml Conclusion
There is a higher yield of cells in the initial 4 ml of aspirate compared to the last 4 ml of marrow extracted

EXAMPLE 3

Aftercare and Controlled Exercise Programme After Stem Cell Therapy

Injury: Superficial digital flexor tendonitis

| Level | Minimum weeks after injury | Duration and nature of exercise |
| --- | --- | --- |
| 0 | 0–2 | Box rest with bandaging |
|  | Between weeks 1 and 2 | Repeat ultrasound examination at the RVC |
| 1 | 3–4 | 10 minutes walking in hand; maintain stable bandaging |
|  | 5–6 | 20 minutes walking in hand; maintain stable bandaging |
|  | 7–8 | 30 minutes walking in hand; maintain stable bandaging |
|  | Between weeks 7 and 8 | Repeat ultrasound examination at the RVC |
| 2 | 9–12 | 40 minutes walking and 5 minutes trotting daily; can be ridden |
|  | 13–16 | 35 minutes walking and 10 minutes trotting daily |
|  | 17–24 | 30 minutes walking and 15 minutes trotting daily |
|  | 25–28 | 25 minutes walking and 20 minutes trotting daily |
|  | 29–32 | 15 minutes walking and 30 minutes trotting daily |
|  | Between weeks 31 and 32 | Repeat ultrasound examination at the RVC |
| 3 | 33–36 | 45 minutes exercise daily with slow canter up to 1 mile twice weekly |
|  | 37–40 | 45 minutes exercise daily with slow canter up to 1.5 mile twice weekly |
|  | 41–44 | 45 minutes exercise daily with one 3 furlong gallop three times a week |
|  | 45–48 | 45 minutes exercise daily with one 6 furlong gallop three times a week |

-continued

| Level | Minimum weeks after injury | Duration and nature of exercise |
|---|---|---|
|  | 49–52 | Increase exercise level gradually to full race/competition training |
|  | Between weeks 51 and 52 | Repeat ultrasound examination at the RVC |
| 4 | From 52 weeks | Full race/competition training |

The ultrasound re-examinations shown are the minimum number - further examinations can be performed as necessary.

This exercise programme may be altered (shortened or lengthened) depending on the progression of the case.

EXAMPLE 4

Treatment Using Direct Bone Marrow Injection Subsequently Caused Ossification

Veterinary Report: 1
Subject: Case No. 333942
"Setta", a 10 yo TB grey mare
Date of Examination: $6^{th}$-$19^{th}$ Jun. 2002
HISTORY: The above pony was referred to the Royal Veterinary College for a bone marrow injection of its superficial digital flexor tendon injury on the left fore.
PHYSICAL EXAMINATION: On initial examination there was only mild thickening to the left fore superficial digital flexor tendon in the mid metacarpal region, although there was still a mild pain response to palpation. In addition, I felt there was some mild thickening of the superficial digital flexor tendon in the mid metacarpal region of the right forefoot.
ULTRASONOGRAPHY: Ultrasonography revealed a large core lesion on the left fore SDFT, occupying about 55% of the cross-sectional area of the tendon at the maximum injury zone (between levels 3 and 4). This lesion extended through most of the length of the metacarpal region. On the right fore there was also a core lesion, but this was much smaller and was restricted to levels 3 and 4. It is not unusual for bilateral tendinitis to be present. The ultrasonographic changes were consistent with the history of a four-week duration of injury.

This case was resolving nicely under conservative management, however, the extent of the lesion meant that it was certainly not a great prognosis for return to high level exercise. The various pros and cons of considering a bone marrow injection were discussed, the rationale being to deliver the mesenchymal stem cells, with or without associated growth factors, which may improve the overall healing of tendon/ligament lesions.
SURGERY: Following extensive discussions with the owner, it was decided that we would try the bone marrow injection in this case. This was performed on the $7^{th}$ Jun. 2002, and bone marrow was obtained from the sternebrae under general anaesthesia. We modified the previously described technique from the States, where large volumes of bone marrow are obtained from the sternebrae and injected into the tendon. There are two reasons why the technique was modified. First of all, large volumes of fluid will cause considerable disruption to an already minimally enlarged tendon, which I felt would be counter-productive. But in addition, there is some evidence from work being performed at the Institute of Orthopaedics at Stanmore, to suggest that most of the mesenchymal stem cells are present in the first few mls of a bone marrow aspirate. Therefore we took separate bone marrow aspirates from separate sternebrae in 2 ml aliquots, and these were injected into both the left and right fore superficial digital flexor tendon through multiple stab incisions. In total 6 mls of bone marrow aspirate were injected into the left fore SDFT core lesion, and 4 mls into the right fore. SDFT. The horse recovered well from GA and the limbs remained bandaged to prevent any post-operative swelling.
CLINICAL PROGRESS: Two post-operative scans showed that the injections had been accurately placed within the core lesion of both limbs. There was somewhat increased heterogeneity to the lesions, but they were not increased in size, which was encouraging and supported the decision not to use large volumes. There was some peritendinous swelling, although this was minimal, the cosmetic appearance of the tendon at this stage was very pleasing.
DISCHARGE INSTRUCTIONS: The horse was discharged on the Jun. $19^{th}$ June and is due to return for a follow up scan within the next few days.
Veterinary Report: 2
Date of Examination: 1 Aug. 2002
HISTORY: The horse had suffered a superficial digital flexor tendinitis, which had been treated with a bone marrow injection on the $7^{th}$ Jun. 2002. This examination is therefore at 8 weeks post-treatment. The horse is currently receiving walking out in hand for a variable amount, between 10-30 minutes per day.
GAIT EVALUATION: Setta was sound at the walk, but had a slightly reduced extension of the left metacarpophalangeal joint. She exhibited a $\frac{1}{10}^{th}$ left forelimb lameness at the trot in a straight line, with some mild discomfort when turned. In view of the absence of shoes, this may be due to foot soreness.
PHYSICAL EXAMINATION: There was only mild swelling to the metacarpal region of the left forelimb. There was minimal swelling on the right fore. There was no evidence of oedema and the tendon borders were well defined and supple to palpation. A mild response was initiated by digital pressure over the flexor tendons on both forelimbs.
ULTRASONOGRAPHY: Ultrasound examination showed that the core lesions were filling in on both forelimbs; however, this tissue did not exhibit a strong striated pattern at this time. There was no increase in the previously observed mineralised area in the left fore SDFT, however there was one small area proximal to this that may be developing some mineralisation. There is no shadowing at present, and it is a very small pinpoint area, but this will be followed carefully in future.
COMMENTS AND RECOMMENDATIONS: Progress of this horse is good; certainly the treatment does not appear to have made the situation any worse, and the core lesion is filling in well. It is difficult to know whether this is any more rapid or better quality than without the bone marrow injection, as only time will tell as the tissue matures.
Veterinary Report: 3
Date of Examination: 2 Jun. 2003
HISTORY: This pony had suffered a superficial digital flexor tendonitis on the left forelimb in May 2002. It had been admitted to the Royal Veterinary College Equine Referral Hospital on the 6Jun. 2002 for intralesional treatment with bone marrow aspirated from the sternum and injected directly into the tendon of both the left and right forelimbs. This was performed under general anaesthesia. Since then the horse had been re-examined on the 1Aug. 2002, which was six weeks or so after treatment. At this stage there was minimal swelling to the metacarpal region of the SDFT on the left forelimb. The area of mineralisation in the SDFT which had been observed prior to treatment, was no bigger, however, there was an extra area that looked a little bit suspicious of developing some mineralisation. The horse had no further re-examinations until the 2Jun. 2003. The pony is back playing polo at present with no obvious problems.

GAIT EVALUATION: The pony was sound at the walk and trot in a straight line.

CLINICAL EXAMINATION: There was subtle enlargement to the superficial digital flexor tendon in the mid metacarpal region in the left fore, but there was no significant pain on palpation. However, there did appear to be an increase in the stiffness on the left and right SDFT's, with the left fore being more marked. Examination on the lunge on a hard surface revealed minimal lameness. Flexion tests, however, were positive on both right and left forelimbs, exacerbating the lameness to ³⁄₁₀ths and ²⁄₁₀ths respectively.

ULTRASONOGRAPHIC EXAMINATION: This revealed the presence of extensive mineralisation within the left fore metacarpal region of the superficial digital flexor tendon, with multiple shadowing artefacts. It is difficult to assess the quality of the rest of the healing tendon because of this shadowing created by these artefacts. There was a small degree of mineralisation also present in the right fore.

RADIOGRAPHIC EXAMINATION: Lateromedial radiographs were obtained of both metacarpal regions. This revealed intratendinous mineralisation within the left fore superficial digital flexor tendon, but no evidence of any mineralisation detected radiographically in the right fore.

SUMMARY: It would appear that the mineralisation has advanced considerably in the left fore SDFT, most likely a consequence of the injection of bone marrow. The appearance of these tendons is disappointing, although it is obviously not compromising the animal's ability at playing polo at the moment.

The modification to use the cultured cells as an alternative way of providing the necessary cells for repair in SDFT tendinitis is considered to reduce the risk of mineralisation.

REFERENCES

Caplan, A. I. and Bruder, S. P. (2001) Mesenchymal stem cells: building blocks for molecular medicine in the 21st century. *Trends Mol. Med.* 7, 259-264.

Carter, D. R., Beaupre, G. S., Giori, N. J., and Helms, J. A. (1998) Mechanobiology of skeletal regeneration. 1: *Clin Orthop* October 1998; (355 Suppl): S41-55.

Cauvin, E. R. J. (2001) An investigation into the roles of transforming growth factor-beta (TGFβ) in the development, adaptation, and repair of equine tendons. PhD thesis, University of London.

Dahlgren, L. A., Nixon, A. J. and Brower-Toland, B. D. (2002) Effects of beta-aminopropionitrile on equine tendon metabolism in vitro and on effects of insulin-like growth factor-I on matrix production by equine tenocytes. *Am. J. Vet. Res.* 62, 1557-1562.

Dowling, B. A., Dart, A. J., Hodgson, D. R. and Smith, R. K. (2000) Superficial digital flexor tendonitis in the horse. *Equine vet. J* 32, 369-378.

Dyson, S. J., Arthur, R. M., Palmer, S. E. and Richardson, D. (1995) Suspensory ligament desmitis. *Vet. Clin. North Am. Equine Practnrs.* 11, 177-215.

Dyson, S. J. (2000) Proximal suspensory desmitis in the forelimb and the hindlimb. *Proc. Am. Ass. Equine Practnrs.* 46, 137-142.

Genovese, R. L. (1992) Sonographic response to intralesional therapy with beta-aminoproprionitrile fumarate for clinical tendon injuries in horses. *Proc. Am. Ass. Equine Practnrs.* 38, 265-272.

Herthel, D. J. (2001) Enhanced suspensory ligament healing in 100 horses by stem cells and other bone marrow components. *Proc. Am. Ass. Equine Practnrs.* 47, 319-321.

Hildebrand, K. A., Jia, F. and Woo, S. L. (2002) Response of donor and recipient cells after transplantation of cells to the ligament and tendon. *Microsc. Res. Tech.* 58, 34-38.

Rickard, D. J., Kassem, M., Hefferan, T. E., Sarkar, G., Spelsberg, T. C. and Lawrence Riggs, B. (1996) Isolation and characterisation of osteoblast precursor cells from human bone marrow. *J. Bone Min. Res.* 11, 312-324.

Reef, V. B., Genovese, R. L. and Davis, W. M. (1997) Initial long term results of horses with superficial digital flexor tendonitis treated with intralesional beta-aminoproprionitrile fumarate. *Proc. Am. Ass. Equine Practnrs.* 43, 301-305.

Reef, V. B., Genovese, R. L., Byrd, J. W., Reed, K. P. and Davis, W. M. (1996) Treatment of superficial digital flexor tendon injuries with beta-aminoproprionitrile (BAPN-F): sonographic evaluation of early tendon healing and remodelling. In Proceedings of the First Dubai International Equine Symposium. The Equine Athlete: Tendon. Ligament, and Soft Tissue Injuries. Rantanen, N. W. and Hauser, M. L. (Eds.), pp. 423-430. Dubai, M. R. Rantanen Design.

Smith, R. K. W., Jones, R. and Webbon, P. M. (1994). The cross-sectional areas of normal equine digital flexor tendons determined ultrasonographically. *Equine vet. J.* 26, 460-465.

Young, R. G., Butler, D. L., Weber, W., Caplan, A. I., Gordon, S. L. and Fink, D. J. (1998) Use of mesenchymal stem cells in a collagen matrix for Achilles tendon repair. *J. Orthop. Res.* 16, 406-413.

Woo, S. L., Hildebrand, K., Watanabe, N., Fenwick, J. A., Papageorgiou, C. D. and Wang, J. H. (1999) Tissue engineering of ligament and tendon healing. *Clin. Orthop.* 367 Suppl., S312-323.

The invention claimed is:

1. A method of treating a soft skeletal tissue injury in a patient, wherein the soft skeletal tissue injury is a tendon or ligament injury, the method comprising: isolating bone marrow cells comprising mesenchymal stem cells and culturing the bone marrow cells in vitro to generate a composition enriched for mesenchymal stem cells and administering to the tendon or ligament injury of the patient the composition enriched for mesenchymal stem cells in a liquid suspension of bone marrow supernatant, wherein said administering promotes regeneration of the tendon or ligament at the site of the tendon or ligament injury.

2. The method according to claim 1 wherein the soft skeletal tissue injury is strain induced.

3. The method according to claim 1 wherein the patient is a mammal.

4. The method according to claim 3 wherein the mammal is a human or a non-human mammal.

5. The method according to claim 4 wherein the non-human mammal is selected from the group consisting of horses, dogs and camels.

6. The method according to claim 1 wherein the patient is a horse.

7. The method according to claim 1 wherein the patient is a horse or a camel and the soft skeletal tissue is selected from the group consisting of superficial digital flexor tendon (SDFT), suspensory ligament, deep digital flexor tendon, cruciate ligament, and accessory ligament of the deep digital flexor tendon.

8. The method according to claim 1 wherein the patient is a dog and the soft skeletal tissue is selected from the group consisting of Achilles tendon, cruciate ligament, and flexor tendon.

9. The method according to claim 1 wherein the patient is a human and the soft skeletal tissue is selected from the group consisting of Achilles tendon, quadriceps tendon, rotator cuff, medial and lateral epicondylitis, and cruciate ligament.

10. The method according to claim 1 wherein the mesenchymal stem cells are allogenic.

11. The method according to claim 1 wherein the mesenchymal stem cells are autologous.

12. The method according to claim 11 wherein the mesenchymal stem cells are derived from bone marrow of the patient.

13. The method according to claim 1 wherein the liquid suspension of mesenchymal stem cells is injected.

14. The method according to claim 1 wherein the tendon or ligament injury is cleansed of damaged tissue and any early repair scar tissue starting to form at the tendon or ligament injury before administration of the composition of mesenchymal stem cells.

15. The method according to claim 1 wherein the soft skeletal tissue injury comprises a cavity, or a lesion that can be closed to form a cavity, for retaining the composition.

16. The method according to claim 1 wherein the composition comprises a gelling agent.

17. The method of claim 1, wherein the soft skeletal tissue injury is percutaneous or subcutaneous.

18. The method of claim 1, wherein the soft skeletal tissue injury is a natural subcutaneous strain induced injury in a tendon or ligament selected from the group consisting of superficial digital flexor tendon (SDFT), suspensory ligament, deep flexor tendon, deep digital flexor tendon (DDFT), accessory ligament of the deep digital flexor tendon, cruciate ligament, Achilles tendon, flexor tendon, quadriceps tendon, rotator cuff, and lateral or medial epicondylitis.

19. A method of treating a soft skeletal tissue injury in a patient, wherein the soft skeletal tissue injury is a tendon or ligament injury, the method comprising: isolating a bone marrow aspirate comprising bone marrow cells; culturing the bone marrow cells in vitro to generate a composition comprising an enriched concentration of mesenchymal stem cells in liquid suspension media, wherein the enriched concentration of mesenchymal stem cells is at least two-fold enriched relative to that of the bone marrow aspirate; and administering the composition comprising the enriched concentration of mesenchymal stem cells to the tendon or ligament injury of the patient, wherein said administering promotes repair of the tendon or ligament at the site of the tendon or ligament injury.

20. The method of claim 19, wherein the liquid suspension media comprises one or more of platelet rich plasma, bone marrow supernatant, serum, plasma, growth factors, differentiation factors, regeneration factors, cytokines or cartilage oligomeric matrix protein.

21. The method of claim 19, wherein the mesenchymal stem cells are enriched in vitro by at least one passage of the bone marrow cells in culture.

22. The method of claim 20, wherein the liquid suspension media comprises plasma or serum with the addition of one or more growth factors, differentiation factors or regeneration factors.

23. The method of claim 22, wherein the additional growth factors, differentiation factors or regeneration factors comprise one or more of TGF beta, IGF 1, IGF 2, PDGF, FGF, or COMP.

* * * * *